United States Patent
Laugharn, Jr. et al.

(10) Patent No.: US 10,093,955 B2
(45) Date of Patent: Oct. 9, 2018

(54) ACOUSTIC ENERGY MEDIATION OF GENETIC FRAGMENTATION

(71) Applicant: Covaris, Inc., Woburn, MA (US)

(72) Inventors: James A. Laugharn, Jr., Winchester, MA (US); Hamid Khoja, Rancho Santa Margarita, CA (US)

(73) Assignee: Covaris, Inc., Woburn, MA (US)

( * ) Notice: Subject to any disclaimer, the term of this patent is extended or adjusted under 35 U.S.C. 154(b) by 0 days.

(21) Appl. No.: 14/881,632

(22) Filed: Oct. 13, 2015

(65) Prior Publication Data

US 2016/0102329 A1    Apr. 14, 2016

Related U.S. Application Data

(60) Provisional application No. 62/063,683, filed on Oct. 14, 2014.

(51) Int. Cl.

| | |
|---|---|
| *C12P 19/34* | (2006.01) |
| *C12Q 1/68* | (2018.01) |
| *C12Q 1/6806* | (2018.01) |
| *B01F 11/02* | (2006.01) |
| *B01F 13/00* | (2006.01) |
| *G01N 1/28* | (2006.01) |
| *B01L 3/00* | (2006.01) |

(52) U.S. Cl.
CPC ............ *C12P 19/34* (2013.01); *B01F 11/0283* (2013.01); *B01F 13/0052* (2013.01); *C12Q 1/6806* (2013.01); *G01N 1/286* (2013.01); *B01L 3/5082* (2013.01)

(58) Field of Classification Search
None
See application file for complete search history.

(56) References Cited

U.S. PATENT DOCUMENTS

| | | | |
|---|---|---|---|
| 6,159,736 A * | 12/2000 | Reznikoff | C12N 9/22 435/455 |
| 6,719,449 B1 | 4/2004 | Laugharn, Jr. et al. | |
| 6,948,843 B2 | 9/2005 | Laugharn, Jr. et al. | |
| 2009/0317884 A1 | 12/2009 | Laugharn, Jr. | |

FOREIGN PATENT DOCUMENTS

| | | |
|---|---|---|
| WO | WO 2008016691 A2 | 2/2008 |
| WO | WO 2009103068 A1 | 8/2009 |
| WO | WO 2010048605 A1 | 4/2010 |
| WO | WO 2014088694 A1 | 6/2014 |

OTHER PUBLICATIONS

Head, S. R. et al., "Library construction for next-generation sequencing: overviews and challenges," Biotechniques, Informa Healthcare, US, vol. 56, No. 2, Feb. 1, 2014, pp. 61-64, 66, 68.
International Search Report and Written Opinion dated Jan. 13, 2016 for corresponding Application No. PCT/US2015/055319.
Knierim, E. et al., "Systematic Comparison of Three Methods for Fragmentation of Long-Range PCR Products for Next Generation Sequencing," PLOS ONE, vol. 6, No. 11, Nov. 30, 2011, p. e28240.
Marine, R. et al., "Evaluation of a transposase protocol for rapid generation of shotgun high-throughput sequencing libraries from nanogram quantities of DNA," Applied and Environmental Microbiology, American Society for Microbiology, vol. 77, No. 22, Nov. 1, 2011, pp. 8071-8079.
Picelli, S. et al., "Tn5 transposase and tagmentation procedures for massively scaled sequencing projects," Genome Research, vol. 24, No. 12, Jul. 30, 2014, pp. 2033-2040.
Quail, M. A. et al., "Evaluation and optimisation of preparative semi-automated electrophoresis systems for Illumina library preparation," Electrophoresis, vol. 33, No. 23, Dec. 12, 2012, pp. 3521-3528.
Tseng, Q. et al., "Fragmentation of DNA in a sub-microliter microfluidic sonication device," Lab on a Chip, vol. 12, No. 22, Jan. 1, 2012, p. 4677.
Adey, A. et al., "Rapid, low-input, low-bias construction of shotgun fragment libraries by high-density in vitro transposition." Genome Biol 11: R119, 2010.
Lamble, S. et al., "Improved workflows for high throughput library preparation using the transposome-based nextera system." BMC Biotechnology 2013 13:104.
Solonenko, S.A., et al., "Sequencing platform and library preparation choices impact viral metagenomes." BMC Genomics 2013 14:320.

\* cited by examiner

*Primary Examiner* — Nancy A Treptow
(74) *Attorney, Agent, or Firm* — Wolf, Greenfield & Sacks, P.C.

(57) ABSTRACT

Method and apparatus for controlling acoustic treatment of a sample to mediate a tagmentation process used on double stranded DNA.

16 Claims, 4 Drawing Sheets

FIG. 1

ACOUSTIC ENERGY MEDIATION OF GENETIC FRAGMENTATION

CROSS REFERENCE TO RELATED APPLICATION

This application claims the benefit of U.S. Provisional Application No. 62/063,683, filed Oct. 14, 2014, which is hereby incorporated by reference in its entirety.

BACKGROUND

1. Field of the Invention

Systems and methods for processing of samples with acoustic energy are generally disclosed.

2. Related Art

Acoustic energy-based sample processing devices, such as Adaptive Focused Acoustic apparatuses made by Covaris of Woburn, Mass., are effective for homogenization and disruption of biological tissues, cells and other sample material. With such devices, a controlled acoustic field enables repeatable processes to be developed which often result in higher recovery of target molecules. Such target molecules may be, for example, DNA, RNA, proteins, and the like. Target molecules or other materials may be contained as samples within a vessel.

SUMMARY OF INVENTION

Tagmentation is a process in which a hyperactive mutant of the Tn5 transposase is used to incorporate a synthetic oligonucleotide into double stranded DNA, essentially carrying out a cut/paste procedure in which the double stranded DNA is cut, and synthetic sequence is inserted. Its utility in generating libraries for next generation sequencing (NGS) systems was first described in a paper by Andrew Adey et al. in 2010 (Adey A, Morrison H G, Asan, Xun X, Kitzman J O, Turner E H, Stackhouse B, MacKenzie A P, Caruccio N C, Zhang X, et al. *Rapid, low-input, low-bias construction of shotgun fragment libraries by high-density in vitro transposition.* Genome Biol 11: R119, 2010.) In commercially available products such as Nextera from Illumina, and MuSeek from Thermo Scientific, the transposase inserts NGS system-specific adaptor oligos in the double stranded DNA sample, and subsequent limited PCR is used to enrich fragments containing the desired adaptors and barcode indices on either end of the DNA fragments.

The inventors have appreciated that the known tagmentation process has some well-known limitations, including:
  G+C bias inherent in transposase-mediated fragmentation;
  Insertion bias towards AT rich region containing similar insertion nucleic acid sequences described for TN5 transposases;
  The process is highly sensitive to the DNA input concentration, requiring precise quantification upstream;
  DNA fragments distribution after tagmentation is wide, thus limiting library yield after size selection.

To address at least some of these limitations, the inventors have developed a tagmentation process that is mediated by acoustic energy. In at least some embodiments, acoustic energy can be used to fragment double stranded DNA having a relatively long base pair length, e.g., in excess of 3000 bp, e.g., 10000 bp or more. This fragmentation can have one or more benefits, such as reducing viscosity of the DNA sample which can enhance enzymatic activity of the tagmentation process. The acoustic energy can also have other benefits, such as shearing double stranded DNA to a smaller fragment size under 3000 bp, e.g., 1000 bp to 1500 bp. This may help create a narrower DNA fragmentation size after the tagmentation process, thereby enhancing the library yield. In other embodiments, the acoustic energy treatment may randomly shear segments of double stranded DNA material in GC and AT rich regions, and in regions having long repeat portions, so as to form fragments of the double stranded DNA material having a base pair length less than 3000 bp. This may help reduce the G+C bias inherent in transposase-mediated fragmentation and/or insertion bias towards AT rich regions containing similar insertion nucleic acid sequences described for TN5 transposases. In yet other embodiments, acoustic energy treatment may reduce a transposase concentration required to successfully perform the tagmentation process, e.g., because the DNA fragmentation caused by the acoustic treatment and/or mixing caused by the acoustic treatment may enhance enzymatic activity of the transposase.

In one aspect of the invention, a method for processing a sample containing genomic material includes providing a sample in a vessel, the sample including double stranded DNA material with segments having a base pair length in excess of a starting base pair length. In some cases, the starting base pair length may be greater than 3000 bp or more, e.g., more than 10000 bp or 48000 bp. The sample may be subjected to acoustic energy to cause shearing of the segments of double stranded DNA material in the sample to form fragments of the double stranded DNA material having a final base pair length, the starting base pair length being two or more times the final base pair length. For example, the fragments of DNA material created by acoustic energy treatment may have a base pair length of less than or about 3000 bp, e.g., 1000 to 1500 bp. A hyperactive mutant of Tn5 transposase and oligonucleotide material may be provided with the fragments of double stranded DNA material to cut the fragments of double stranded DNA material with the Tn5 transposase and insert oligonucleotide material into the fragments of double stranded DNA material at areas cut by the Tn5 transposase. The transposase and oligonucleotide material may be provided with the sample before or after subjecting the sample to acoustic energy to shear the DNA into fragments. In some embodiments, the sample may be subjected to acoustic energy to mix the hyperactive mutant of Tn5 transposase, oligonucleotide material, and the fragments of double stranded DNA material after the step of subjecting the sample to acoustic energy to cause shearing. This may help enhance the enzymatic and oligonucleotide insertion process.

In another aspect of the invention, a method for processing a sample containing genomic material includes providing a sample in a vessel, the sample including double stranded DNA material with segments having a starting base pair length, and the sample having a starting viscosity. The sample may be subjected to acoustic energy to reduce a viscosity of the sample to a reduced viscosity that is less than the starting viscosity. The acoustic energy treatment may also cause shearing of the segments of double stranded DNA material in the sample to form fragments of the double stranded DNA material having a base pair length of less than the starting base pair length. A hyperactive mutant of Tn5 transposase and oligonucleotide material may be provided with the fragments of double stranded DNA material to cut the fragments of double stranded DNA material with the Tn5 transposase and insert oligonucleotide material into the fragments of double stranded DNA material at areas cut by the Tn5 transposase. The reduction of viscosity of the sample caused by acoustic energy treatment may enhance the enzymatic activity of the transposase, e.g., because steric hindrance presence in higher viscosity solutions may be reduced with reduced sample viscosity. As a result, the tagmentation process may be performed more efficiently. In some embodiments, a concentration of transposase needed to perform the tagmentation process may be significantly reduced as compared to tagmentation processes performed without the use of acoustic energy. The hyperactive mutant of Tn5 transposase and oligonucleotide material may be provided with the fragments of double stranded DNA material before or after the step of subjecting the sample to acoustic energy to shear the DNA segments, and in some cases, acoustic energy treatment may be used to mix the hyperactive mutant of Tn5 transposase, oligonucleotide material, and the fragments of double stranded DNA material after the step of subjecting the sample to acoustic energy to cause shearing. The acoustic energy used to mix may be provided at a lower power than the acoustic energy used to shear the DNA segments.

In another aspect of the invention, a method for processing a sample containing genomic material includes providing a sample in a vessel, the sample including double stranded DNA material with segments having a base pair length in excess of 3000 bp. The segments of double stranded DNA material may be randomly sheared in GC and AT rich regions, and in regions having long repeat portions, to form fragments of the double stranded DNA material having a base pair length less than 3000 bp. For example, in some embodiments, acoustic energy may be employed to randomly shear the DNA segments. A hyperactive mutant of Tn5 transposase and oligonucleotide material may be provided with the fragments of double stranded DNA material to cut the fragments of double stranded DNA material with the Tn5 transposase and insert oligonucleotide material into the fragments of double stranded DNA material at areas cut by the Tn5 transposase.

Generally speaking, shearing of DNA and other genomic fragments using acoustic treatment is known from U.S. Patent Publication 2009/0317884. For example, U.S. Patent Publication 2009/0317884 discloses placing DNA fragments having a base pair length of 10 kbp and up into a 50-100 microliter vessel along with an energy director in the form of a polymer rod or bead, and acoustically treating the DNA fragments so as to shear the DNA fragments into smaller fragment sizes of about 3 kbp. Other acoustic energy treatment protocols have been provided by Covaris, Inc. of Woburn, Ma. For example, DNA shearing to base pair sizes between about 150 to 1500 bp may be performed using a Covaris 5220 system by employing a peak incident power (PIP) between 140 and 175 Watts, a 2 to 10% duty factor, 200 cycles per burst and a treatment time of 15 to 430 seconds. Sample volume may be 50 or 130 microliters and may be held in a Covaris microTUBE. (The energy applied to a sample via acoustic energy is measured in Joules and given by the product of peak incident power (PIP in watts) by the duty cycle of the applied energy (DC in percentage terms) by the total processing time (T in seconds) or E=PIP*DC*T).) As will be understood, the acoustic energy employed in such shearing operations is focused acoustic energy such that a focal zone is present at the sample being treated.

Other advantages and novel features of the invention will become apparent from the following detailed description of various non-limiting embodiments when considered in conjunction with the accompanying figures and claims.

BRIEF DESCRIPTION OF THE DRAWINGS

Aspects of the invention are described with reference to the following drawings in which numerals reference like elements, and wherein.

DETAILED DESCRIPTION

Aspects of the invention are not limited in application to the details of construction and the arrangement of components set forth in the following description or illustrated in the drawings. Other embodiments may be employed and aspects of the inventions may be practiced or be carried out in various ways. Also, the phraseology and terminology used herein is for the purpose of description and should not be regarded as limiting.

Acoustic treatment systems can be useful for the homogenization and disruption of biological tissues, cells and other sample material, with the end goal of recovering target molecules from the sample material, such as DNA, RNA, proteins, and the like. In addition, such systems may be used along with aspects of the invention for DNA and/or other genomic fragment shearing, e.g., to reduce the base pair length of DNA fragments from 1,000s or 10,000s of base pairs to lengths of 200-1000 base pairs. As described in more detail below, acoustic energy, and specifically focused acoustics, can be useful in mediating a tagmentation process. Generally speaking the inventors have found the following features and benefits to employing focused acoustics with a tagmentation process:

Utilizing acoustic energy to randomly shear DNA to an average size of around 1-1.5 kb may:
  a. Increase the complexity of the resulting library by randomly shearing the genomic DNA in GC and AT rich regions, as well as long stretches of repeats, leading to reduced G+C bias of the library.
  b. The 1-1.5 kb fragments will render the fragments more accessible to the transposases since long stretches of low concentration genomic DNA are converted into higher concentration, partially fragmented DNA. The resultant transposase-processed DNA should have a tighter size distribution as compared to genomic DNA processed by a transposase alone.

Carrying out the tagmentation reaction in the presence of acoustic energy, e.g., of relatively low power as compared to acoustic energy used for shearing, will provide efficient gentle mixing of the reaction components. As a result, the tagmentation reaction may experience:
  a. An increase in the rate of sample/enzyme interaction leading to a more efficient tagmentation reaction. This can reduce the concentration of transposase required per reaction further reducing the cost of library preparation.

b. Further reduction in the distribution of DNA fragments generated by tagmentation as a result of efficient mixing of the components during the tagmentation reaction.

c. Better control over the tagmentation fragment size. This will allow for greater utility of tagmentation in applications requiring longer fragment inserts.

d. Reduce tagmentation sensitivity to input DNA mass and concentration.

Figure 1:
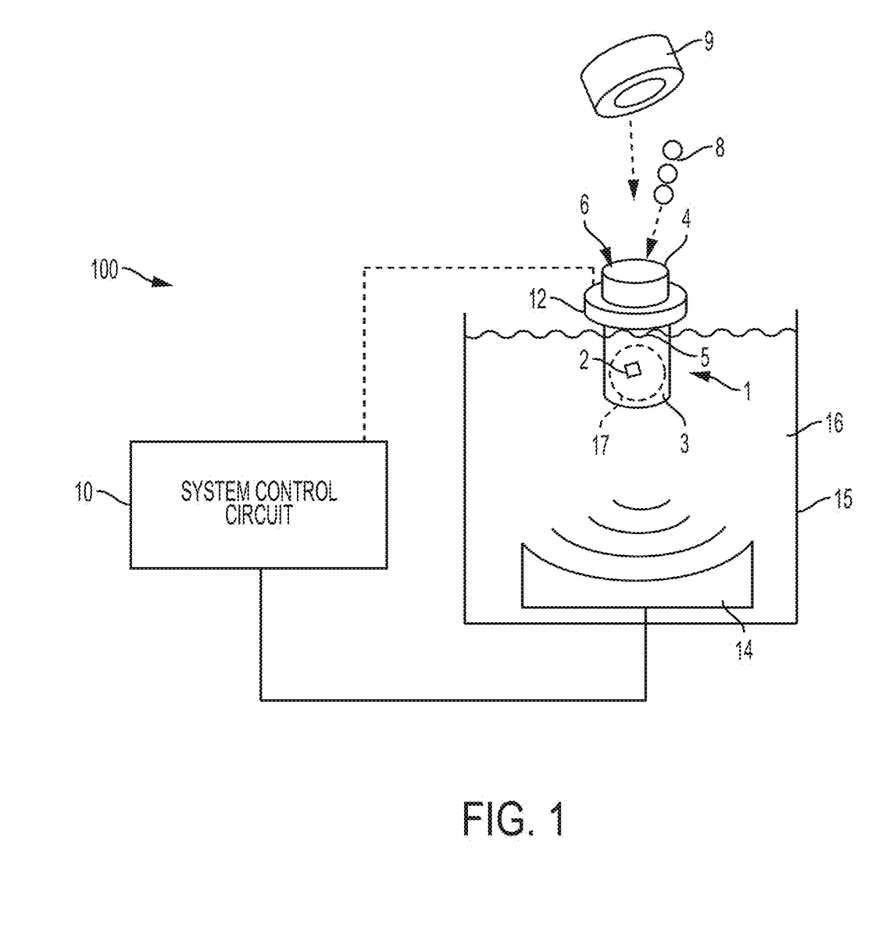
FIG. 1 shows a schematic block diagram of an acoustic treatment system that incorporates one or more aspects of the invention.

FIG. 1 shows a schematic block diagram of an acoustic treatment system 100 that incorporates one or more aspects of the invention and/or can be employed with one or more aspects of the invention. It should be understood that although embodiments described herein may include most or all aspects of the invention, aspects of the invention may be used alone or in any suitable combination with other aspects of the invention. In this illustrative embodiment, the acoustic treatment system 100 includes an acoustic transducer 14 (e.g., including one or more piezoelectric elements) that is capable of generating an acoustic field (e.g., at a focal zone 17) suitable to cause mixing, e.g., caused by cavitation, and/or other affects in a sample 1 contained in a vessel 4. The acoustic transducer 14 may produce acoustic energy within a frequency range of between about 100 kilohertz and about 100 megahertz such that the focal zone 17 has a width of about 2 centimeters or less. The focal zone 17 of the acoustic energy may be any suitable shape, such as spherical, ellipsoidal, rod-shaped, or column-shaped, for example, and be positioned at the sample 1. The focal zone 17 may be larger than the sample volume, or may be smaller than the sample volume, as shown in FIG. 1. U.S. Pat. Nos. 6,948,843 and 6,719,449 are incorporated by reference herein for details regarding the construction and operation of an acoustic transducer and its control.

The vessel 4 may have any suitable size or other arrangement, e.g., may be a glass tube, a plastic container, a well in a microtiter plate, a vial, or other, and may be supported at a location by a vessel holder 12. Although a vessel holder 12 is not necessarily required, the vessel holder 12 may serve to interface with the acoustic processing device so that the vessel 4 and the sample in the vessel is positioned in a known location relative to an acoustic field, for example, at least partially within a focal zone of acoustic energy. In this embodiment, the vessel 4 is a 130 microliter borosilicate glass tube, but it should be understood that the vessel 4 may have other suitable shapes, sizes, materials, or other feature, as discussed more below. For example, the vessel 4 may be a cylindrical tube with a flat bottom and a threaded top end to receive a cap, may include a cylindrical collar with a depending flexible bag-like portion to hold a sample, may be a single well in a multiwell plate, may be a cube-shaped vessel, or may be of any other suitable arrangement. The vessel 4 may be formed of glass, plastic, metal, composites, and/or any suitable combinations of materials, and formed by any suitable process, such as molding, machining, stamping, and/or a combination of processes.

The acoustic treatment system 100 may also include a coupling medium container 15 that is capable of holding a medium 16 (such as water or other liquid, gas, gel, solid, semi-solid, and/or a combination of such components) which transmits acoustic energy from the transducer 14 to the vessel 4. In some embodiments, the acoustic field may be controlled, the acoustic transducer 14 may be moved, and/or the vessel 4 may be moved (e.g., by way of moving a holder 12, such as a rack, tray, platform, etc., that supports the vessel 4) so that the sample is positioned in a desired location relative to the focal zone 17. Also, the holder 12 is not limited to a device like that shown in FIG. 1, and instead may include a rack, slot, tray, gripper element, clamp, box or any other suitable arrangement for holding the vessel, or multiple vessels, in a desired location. For example, the holder 12 may include one or more multi-vessel supports and a rack. Each support may hold a plurality of vessels 4, e.g., a plurality of vessels may be held in a linear array. Each support may include an identifier, such as a barcode, RFID chip, or other component that may be read so as to identify the support and/or vessels 4 associated with the support. The rack may hold multiple supports with vessels and make it easier to physically manipulate or otherwise handle multiple vessels 4, e.g., in an automated processing environment in which one or more robotic devices manipulate vessels for acoustic or other processing. For example, the support may include a strip of material with holes into which each vessel is inserted. The rack may be arranged in the form of a multiwell plate such that vessel bottoms extending below the support may be received into a corresponding opening or well of the plate. The rack may also include an identifier so that the rack and/or supports on the rack can be identified in a automated way, e.g., by a laser scanner, optical camera, RFID tag reader or other arrangement.

To control the acoustic transducer 14, the acoustic treatment system 100 may include a system control circuit 10 that controls various functions of the system 100 including operation of the acoustic transducer 14. For example, the system control circuit 10 may provide control signals to a load current control circuit, which controls a load current in a winding of a transformer. Based on the load current, the transformer may output a drive signal to a matching network, which is coupled to the acoustic transducer 14 and provides suitable signals for the transducer 14 to produce desired acoustic energy. As discussed in more detail below, the system control circuit 10 may control various other acoustic treatment system 100 functions, such as positioning of the vessel 4 and/or acoustic transducer 14, receiving operator input (such as commands for system operation), outputting information (e.g., to a visible display screen, indicator lights, sample treatment status information in electronic data form, and so on), and others.

In this illustrative embodiment, the sample 1 includes DNA segments 2 and a liquid 3, e.g., 15 to 130 microliters of liquid containing 20-30 nanograms of DNA fragments per microliter. (Although the DNA segments 2 are shown schematically as a single block of material, this is for purposes of illustration only. The DNA segments 2 may be dispersed in the liquid 3 and generally will not form a solid mass.) The DNA segments 2 may have a starting base pair length of 3 kbp, 5 kbp, 10 bkp, 48 kbp or more, e.g., such that 90% or more of the DNA fragments have a base pair length over 3 kbp, 5 kbp, etc. Of course, those of skill in the art will appreciate that the sample 1 is not limited to including a liquid 3, as the sample 1 may take any suitable form, such as a solid only form, a gel, a semi-solid, etc.

In at least some embodiments, the sample volume may be less than the volume of the vessel, and thus an interface 5 will separate the sample 1 from a headspace 6 in the vessel, i.e., a gaseous region immediately above the sample 1. This arrangement may cause portions of the sample 1 to be splashed or otherwise ejected from the interface 5 in some conditions, e.g., to adhere to the vessel 4 sidewalls above the interface 5. However, the presence of one or more beads 8 in the sample 1 may reduce splashing or other sample 1 ejection from the interface 5. The beads 8 may function as a nucleation site for cavitation induced by the acoustic energy and cause shear forces created during cavitation bubble collapse to be directed to the surface of the bead, instead of to other portions in the sample. By arranging all portions of the sample within a maximum distance, e.g., 2 mm or less, of a bead surface, all portions of the sample may be positioned suitably near the bead surface (e.g., due to mixing during acoustic treatment) to experience shear or other forces that cause shearing of genomic material.

Thus, in some embodiments, the presence of the bead(s) 8 in the sample 1 having a volume of 1-30 microliters may enable shearing of DNA to occur under lower power or energy conditions than would otherwise be possible. In addition, DNA or other genomic segments may be sheared to lengths much shorter than previously possible under relatively low power or energy conditions. DNA segments having a base pair length of 3 kbp, 5 kbp, 10 bkp, 48 kbp or more may be sheared by acoustic energy having a PIP of 20 watts or less and a duty cycle of 10-20% in 30-200 seconds such that the 90%, 95% or more of the fragments end up with a base pair length of 200-1500 bp. This is a significant and surprising improvement over prior processes.

The bead(s) may have a diameter of about 1-3 mm, with a diameter of 1.57 mm being found particularly effective in genomic shearing with sample volumes around 15 microliters. In some embodiments, three beads 8 having a 1.57 mm diameter have been found particularly useful. Beads made of PTFE have been found effective, although other polymer materials are expected to work as well. Beads having a coarse surface finish, as opposed to a polished surface finish, have been found to be effective in many applications. Generally, the beads are non-buoyant so as to remain immersed in the sample during acoustic processing, but the beads could be formed as part of a vessel wall, be attached to a vessel wall, or be neutrally buoyant. Also, although beads 8 in the illustrated embodiment are shown as spherical in shape, the beads may have a variety of shapes, e.g., like jewelry elements commonly referred to as "beads" have a variety of different shapes and sizes. However, it should be understood that the use of beads 8 is not required, and instead, DNA shearing may be performed in the absence of any beads 8 or other elements in the vessel 4.

The embodiment shown in FIG. 1 also includes a cap 9 that may be used to close the open end of the vessel 4. By capping the open end of the vessel 4, an operator may be able to prevent flow out of/into the vessel 4 and/or prevent contamination of the sample 1 by the outside environment. The cap 9 may engage the vessel 4 in any way, such as by screw thread, interference fit, frictional engagement to the inner or outer surface of the vessel sidewall, etc. The use of a cap 9 is optional, and not required.

Figure 2:
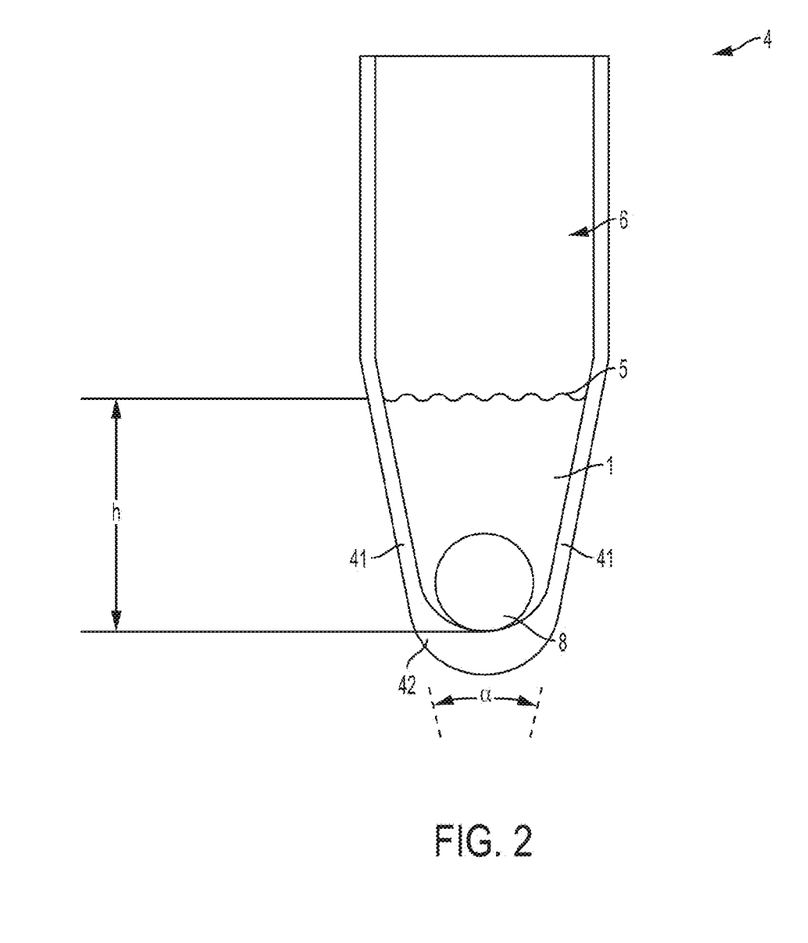
FIG. 2 shows a cross sectional view of a vessel containing a sample that may be used with aspects of the invention.

In one aspect of the invention, a vessel in which genomic material is sheared may have a conically shaped bottom arranged such that the conical walls diverge upwardly from each other at an aperture angle of about 12-20 degrees. For example, FIG. 2 shows an arrangement in which the sidewalls 41 of the vessel 4 diverge from each other at an aperture angle α of about 16 degrees. The sidewalls 41 may be relatively thin, e.g., about 0.25 mm in thickness, so as to reduce interference with acoustic energy and/or enhance heat exchange with the coupling medium 15. The extreme bottom 42 of the vessel may have a partial spherical shape with a radius of about 1-2 mm. The bottom 42 may be thicker than the sidewalls 41 as shown, or may have the same or smaller thickness. The partial spherical bottom may help with recovery of sample after processing, since sample may tend to collect at the bottom, allowing pipetting from the vessel. The sample 1 may have a height h in the vessel 4 of about 3-4 mm as measured from the inner bottom of the vessel to the interface 5.

Figure 3:
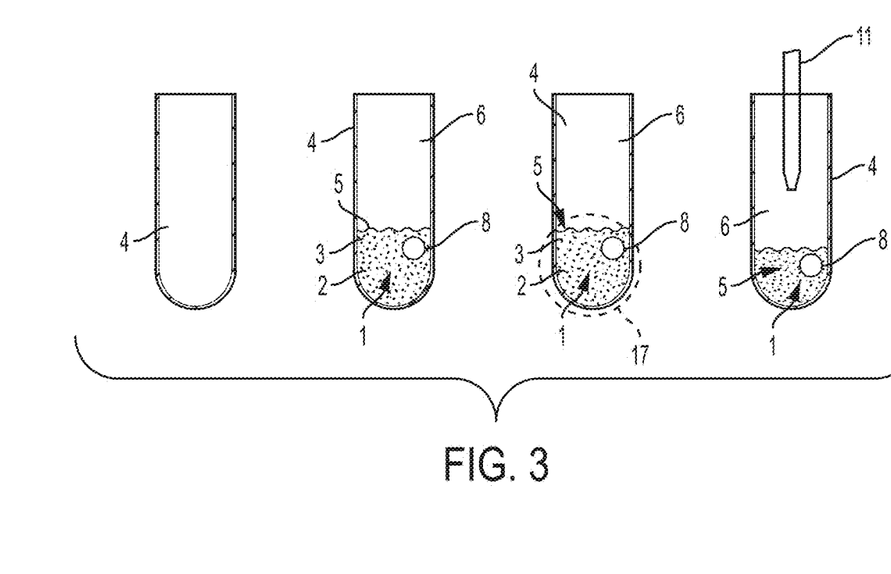
FIG. 3 illustrates schematic steps of a method for performing tagmentation in an illustrative embodiment.

FIG. 3 outlines steps in a method of performing a tagmentation process with genomic material in accordance with aspects of the invention. A vessel 4 is provided having a vessel volume, which may be 50-150 microliters or more (or less). The vessel 4 may be made of glass or a polymer or other material, if suitable. Glass materials may aid in heat transfer to a coupling medium, and some polymer materials have been found to aid in genomic material shearing. The vessel 4 may have a conically-shaped bottom with sidewalls upwardly diverging at an angle of about 12-20 degrees, e.g., as shown in FIG. 2. The extreme bottom of the vessel 4 may have a partial spherical shape. This arrangement has been found particularly useful in shearing DNA in a sample volume of about 15 microliters. Alternately, the vessel 4 may be a cylindrical tube with vertical sidewalls and a flat or spherical bottom, as shown.

Next, a sample 1 containing DNA segments 2 and liquid 3 may be placed in the vessel 4. The sample 1 may have a volume of about 1 to 130 microliters, with a volume of 15 microliters having been found in some examples to be particularly suitable for effective DNA shearing. The sample 1 may have a height in the vessel 4 of about 3-4 mm above the vessel inner bottom. Genomic fragments in the sample may be provided at a concentration of about 20-30 nanograms/microliter, and may have fragment lengths of more than 3 kbp, 5 kbp, 10 kbp, 48 kbp or more. Optionally, one to three polymer beads, e.g., made of PTFE having a diameter of 1-3 mm may be provided in the sample 1 so the beads are immersed in the sample. Providing three spherical PTFE beads having a diameter of about 1.57 mm in a 15 microliter sample has been found particularly suitable for shearing DNA.

Thereafter, the sample 1 may be treated with acoustic energy to shear the DNA segments in the sample 1. The acoustic energy may have a frequency range of between about 100 kilohertz and about 100 megahertz and have a focal zone 17 with a width of about 2 centimeters or less. The focal zone 17 may be positioned so that the entire sample 1 is located in the focal zone 17, or so that a portion of the sample is in the focal zone 17. In some embodiments, the sample may move through the focal zone 17, whether by moving the focal zone 17 relative to the vessel 4 or moving the vessel 4 relative to the focal zone 17. The acoustic energy may have a peak incident power (PIP) of 20 watts or less and a duty cycle of 10-20%. The sample 1 may be treated with the acoustic energy over a time period of 30-200 seconds. As a result, 90%, 95%, 99% or more of the genomic material having a relatively long starting base pair length may be sheared to fragments having a resulting base pair length that is at least one-half or smaller than the starting base pair length, e.g., 1000 to 1500 bp. In some embodiments, 99% or more of the initial genomic material may be sheared to have a base pair length of 1000-1500 bp.

With acoustic energy shearing complete, a hyperactive mutant of Tn5 transposase and oligonucleotide material may be provided with the fragments of double stranded DNA material to cut the fragments of double stranded DNA material with the Tn5 transposase and insert oligonucleotide material into the fragments of double stranded DNA material at areas cut by the Tn5 transposase. The transposase and oligonucleotide material may be provided with the sample by pipette 11 or in other ways, and may be provided before or after subjecting the sample to acoustic energy to shear the DNA into fragments. That is, the DNA segments may be sheared by acoustic energy while in the presence of the transposase and olionucleotide material. In some embodiments, the sample may be subjected to acoustic energy to mix the hyperactive mutant of Tn5 transposase, oligonucleotide material, and the fragments of double stranded DNA material after the sample is exposed to acoustic energy to cause shearing. This may help enhance the enzymatic and oligonucleotide insertion process. In other embodiments, once acoustic energy shearing and tagmentation is complete, other processes may be performed on the sample while in the vessel, such as PCR amplification, stirring, catalyzing, heating, disruption of molecular bonds, or any other appropriate process. Such processes may be performed using acoustic energy, or not, e.g., PCR processing may be performed by a standard thermocycler machine.

A few illustrative examples of DNA shearing and tagmentation processes using methods and systems according to the invention are described below.

Example One

Figure 4:
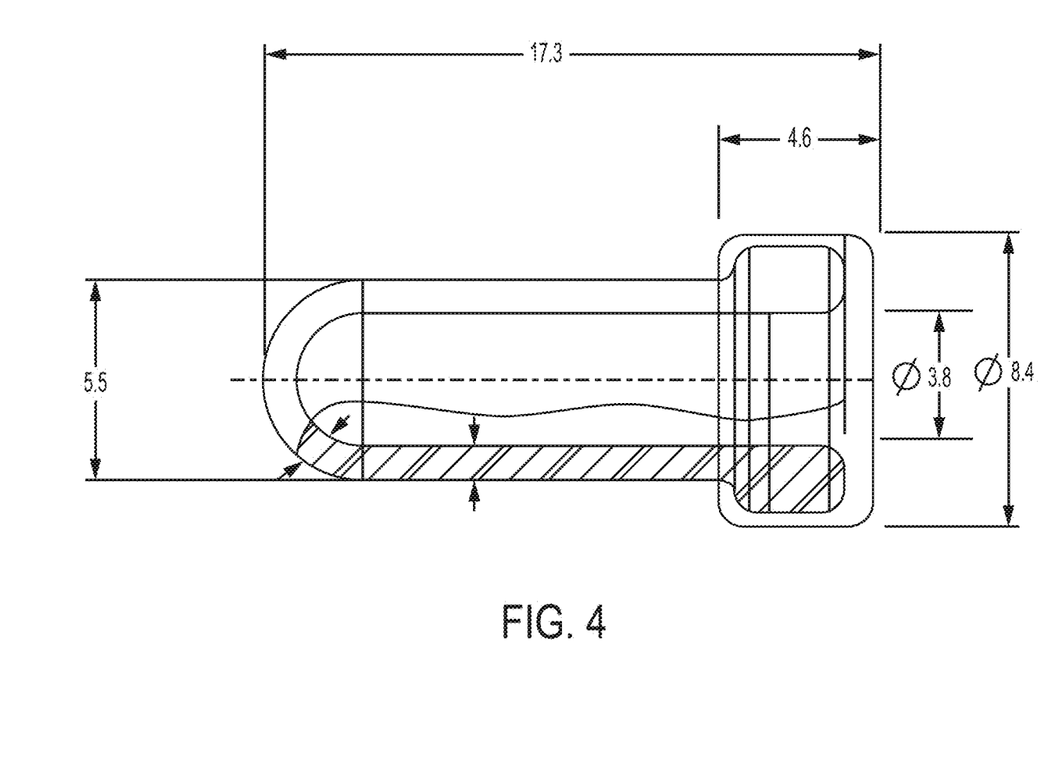
FIG. 4 shows a vessel used to hold a sample in Example One below.

A vessel having a volume of 130 microliters was provided with a 15 microliter sample containing lambda DNA (i.e., DNA fragments having a base pair length of 48 kbp or more) at a concentration of about 28 nanograms/microliter, but may be lower, e.g., down to 7 nanograms/microliter. Three 1.57 mm PTFE beads were provided in the sample as well, and the borosilicate glass vessel having a spherical bottom was closed by a split septum, as shown in FIG. 4. (Dimensions in FIG. 4 are in millimeters.) The sample was acoustically treated using a Covaris S220 ultrasonicator set to provide a PIP of 18 watts, a 20% duty cycle and 50 cycles per burst for 60 seconds. Some splashing of the sample was observed during acoustic treatment. More than 95% of the lambda DNA fragments were sheared to DNA fragments having a length under 1000 bp, with an average base pair length of the sheared DNA being about 336 bp. More than 75% of the sheared DNA had a base pair length of 100-500 bp. Also of note is that more than 96% of the sample was recovered from the vessel after acoustic treatment, and more than 93% of the DNA material initially provided in the vessel was recovered by pipetting. The experiment was repeated 12 times, and a coefficient of variation of less than 4% was determined, i.e., the results of DNA shearing were found to be highly repeatable and consistent. The total energy of about 216 Joules to shear the lambda DNA is far less than expected, and is thought to be due at least in part to the relatively small sample size and the presence of three beads in the sample.

Example Two

Example One was repeated, except that the samples were processed with two 1.57 mm beads and with one 1.57 mm beads. (Processing time for the single bead experiment was increased from 60 seconds to 120 seconds.) In both experiments, more than 90% of the lambda DNA fragments were sheared to DNA fragments having a length under 1000 bp, with an average base pair length of the sheared DNA being about 332 bp for two beads, and about 412 bp for one bead. The coefficient of variation for two beads was about 4.0%, and for one bead was about 7.2% based on 12 repeat experiments for each.

Example Three

Example One was repeated, except that the samples were processed using one 2.36 mm bead, i.e., a larger bead than those used in Examples One and Two. The results are shown in FIG. 7. More than 95% of the lambda DNA fragments were sheared to DNA fragments having a length under 1000 bp, with an average base pair length of the sheared DNA being about 337 bp. The coefficient of variation was about 10.5% based on 12 repeat experiments, i.e., a significant drop in repeatability versus the smaller bead sizes. Recovery of the sample volume was about 80%, also significantly less than that found in the three bead example above.

Example Four

Double stranded DNA having segments with a starting base pair size of about 5000 bp is sheared using a Covaris S220 system and employing a Covaris protocol to shear DNA to a resulting base pair size of about 1500 bp. For example, 2 micrograms of *E. coli* double stranded DNA is provided in a 130 microliter sample including water in a Covaris microTUBE having a 130 microliter volume. A Tris EDTA buffer having a pH of 8.0 is included along with a Covaris microTUBE fiber. The sample is treated with focused acoustic energy from the S220 system employing a peak incident power (PIP) of 140 Watts, a 2% duty factor, 200 cycles per burst and a treatment time of 15 seconds. This treatment shears the double stranded DNA to create fragments having a resulting base pair size of about 1500 bp. Prior to acoustic energy treatment, Dnase I enzyme is used to nick the input DNA sample material using an enzyme concentration of 0.1 to 0.001 units and an incubation time of 5 to 60 minutes. The Dnase I enzyme activity is stopped by adding EDTA in a final concentration of 10 mM to the sample and heating to 70 degrees C. for 15 minutes. After acoustic treatment to shear the DNA, the Nextera XT protocol is followed in which a hyperactive mutant of Tn5 transposase and oligonucleotide material is provided with the fragments of double stranded DNA material to cut the fragments of double stranded DNA material with the Tn5 transposase and insert oligonucleotide material into the fragments of double stranded DNA material at areas cut by the Tn5 transposase. An Agilent Bioanalyzer and associated high sensitivity DNA assay is used to analyze aliquots of sample material for fragment size distribution. A Kapa library quantification kit is used to measure library efficiency.

As described above, the system control circuit 10 may include any suitable components to perform desired control, communication and/or other functions. For example, the system control circuit 10 may include one or more general purpose computers, a network of computers, one or more microprocessors, etc. for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the load current control circuit as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the medium 16, a video camera or other imaging device to capture and analyze image information regarding the vessel 4 or other components, position sensors to indicate positions of the acoustic transducer 14 and/or the vessel 4, and so on), user data input devices (such as buttons, dials, knobs, a keyboard, a touch screen or other), information display devices (such as an LCD display, indicator lights, a printer, etc.), and/or other components for providing desired input/output and control functions.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

What is claimed is:

1. A method for processing a sample containing genomic material, comprising:
   providing a sample in a vessel, the sample including double stranded DNA material with segments having a base pair length in excess of a starting base pair length;
   subjecting the sample to acoustic energy to cause random shearing of the segments of double stranded DNA material in the sample to form fragments of the double stranded DNA material having a base pair length of a final base pair length, the starting base pair length being two or more times the final base pair length; and
   providing a hyperactive mutant of Tn5 transposase and oligonucleotide material with the fragments of double stranded DNA material to cut the fragments of double stranded DNA material with the Tn5 transposase and insert oligonucleotide material into the fragments of double stranded DNA material at areas cut by the Tn5 transposase.

2. The method of claim 1, wherein the step of providing a hyperactive mutant of Tn5 transposase and oligonucleotide material with the fragments of double stranded DNA material occurs before the step of subjecting the sample to acoustic energy.

3. The method of claim 1, further comprising:
   subjecting the sample to acoustic energy to mix the hyperactive mutant of Tn5 transposase, oligonucleotide material, and the fragments of double stranded DNA material after the step of subjecting the sample to acoustic energy to cause shearing.

4. The method of claim 1, wherein the oligonucleotide material includes synthetic oligonucleotides.

5. The method of claim 1, wherein the sample volume is about 15 microliters.

6. The method of claim 1, wherein the vessel volume is about 100 microliters.

7. The method of claim 1, wherein the starting base pair length is in excess of 10000 bp.

8. The method of claim 1, wherein the final base pair length is less than 3000 bp.

9. The method of claim 1, wherein the final base pair length is between 1000 bp and 1500 bp.

10. The method of claim 1, wherein the step of subjecting the sample to acoustic energy reduces a viscosity of the sample so as to enhance enzyme interaction that occurs during the step of providing a hyperactive mutant of Tn5 transposase and oligonucleotide material.

11. The method of claim 1, wherein the subjecting step is performed over a time period of 30-200 seconds.

12. The method of claim 1, wherein the step of providing a hyperactive mutant of Tn5 transposase and oligonucleotide material with the fragments of double stranded DNA material occurs after the step of subjecting the sample to acoustic energy.

13. The method of claim 12, further comprising:
   subjecting the sample to acoustic energy to mix the hyperactive mutant of Tn5 transposase, oligonucleotide material, and the fragments of double stranded DNA material after the step of subjecting the sample to acoustic energy to cause shearing.

14. The method of claim 1, wherein the oligonucleotide material includes synthetic oligonucleotides.

15. A method for processing a sample containing genomic material, comprising:
   providing a sample in a vessel, the sample including double stranded DNA material with segments having a base pair length in excess of 3000 bp;
   subjecting the sample to acoustic energy to cause random shearing of the segments of double stranded DNA material in the sample to form fragments of the double stranded DNA material having a base pair length less than 3000 bp; and
   providing a hyperactive mutant of Tn5 transposase and oligonucleotide material with the fragments of double stranded DNA material to cut the fragments of double stranded DNA material with the Tn5 transposase and insert oligonucleotide material into the fragments of double stranded DNA material at areas cut by the Tn5 transposase, wherein a concentration of the Tn5 transposase is less than that needed to perform a tagmentation process using techniques without acoustic energy treatment.

16. A method for processing a sample containing genomic material, comprising:
   providing a sample in a vessel, the sample including double stranded DNA material with segments having a base pair length in excess of 3000 bp;
   subjecting the sample to acoustic energy to cause random shearing of the segments of double stranded DNA material in the sample to form fragments of the double stranded DNA material having a base pair length less than 3000 bp; and
   providing a hyperactive mutant of Tn5 transposase and oligonucleotide material with the fragments of double stranded DNA material to cut the fragments of double stranded DNA material with the Tn5 transposase and insert oligonucleotide material into the fragments of double stranded DNA material at areas cut by the Tn5 transposase, wherein the fragments of double stranded DNA material having inserted oligonucleotide material have a tighter size distribution than that resulting from standard tagmentation processes performed in the absence of acoustic treatment.

* * * * *